United States Patent [19]

Fünfschilling

[11] 4,395,550

[45] Jul. 26, 1983

[54] TETRAHYDRO-2(1H)-QUINAZOLINONES AND CYCLOHEXENE NITRILES

[75] Inventor: Peter Fünfschilling, Basel, Switzerland

[73] Assignee: Sandoz Ltd., Basel, Switzerland

[21] Appl. No.: 318,480

[22] Filed: Nov. 5, 1981

Related U.S. Application Data

[63] Continuation of Ser. No. 164,048, Jun. 30, 1980, abandoned.

[30] Foreign Application Priority Data

Jul. 5, 1979 [CH] Switzerland .................. 6298/79

[51] Int. Cl.³ .................. C07D 239/82; C07D 239/96; C07C 125/065
[52] U.S. Cl. .................. 544/253; 260/464; 260/465 D; 544/285; 544/286; 544/287
[58] Field of Search .............. 544/253, 285, 286, 287; 260/464, 465 D

[56] References Cited

U.S. PATENT DOCUMENTS

| 2,217,632 | 10/1940 | Wolfe ..................... 260/464 |
| 3,723,432 | 3/1973 | Ott ........................ 544/286 |
| 3,937,705 | 2/1976 | Hardtmann ............. 544/286 |
| 3,996,227 | 12/1976 | Salmond ................ 544/253 |
| 4,065,496 | 12/1977 | Oppolzer ............... 560/115 X |
| 4,171,441 | 10/1979 | Smith .................... 554/286 |

FOREIGN PATENT DOCUMENTS

| 2022470 | 11/1971 | Fed. Rep. of Germany ...... 544/286 |
| 2142317 | 3/1973 | Fed. Rep. of Germany ...... 544/253 |
| 46-37830 | 11/1971 | Japan ................................. 544/285 |
| 48-21955 | 7/1973 | Japan ................................. 544/286 |
| 7114936 | 5/1972 | Netherlands ...................... 544/286 |

OTHER PUBLICATIONS

Mekhtiev et al., J. Org. Chem. U.S.S.R., vol. 5, pp. 1364–1366 (1969).
Kricheldorf, Liebig's Ann. Chem., 1975, pp. 1387–1393 (1975).
Garcia et al., Chemical Abstracts, vol. 78, 124,553n (1973).
Engelhardt et al., Chemical Abstracts, vol. 89, 197196k (1978).

*Primary Examiner*—Donald G. Daus
*Assistant Examiner*—Diana G. Rivers
*Attorney, Agent, or Firm*—Gerald D. Sharkin; Richard E. Vila

[57] ABSTRACT

A process for the production of 4-phenyl-2(1H)-quinazolinones and -4a,5,6,8a-tetrahydro-2(1H)-quinazolinones which comprises introducing the desired phenyl radical into a corresponding quinazolin-2,4(1H,3H)-dione by way of a Grignard reaction and hydrolysis of the resulting product.

9 Claims, No Drawings

TETRAHYDRO-2(1H)-QUINAZOLINONES AND CYCLOHEXENE NITRILES

This is a continuation of application Ser. No. 164,048 filed June 30, 1980, abandoned.

The present invention relates to a process for the production of 4-phenyl-2(1H)-quinazolinones and -4a,5,6,8a-tetrahydro-2(1H)-quinazolinones.

More particularly, this invention provides a process for the production of compounds of formula I,

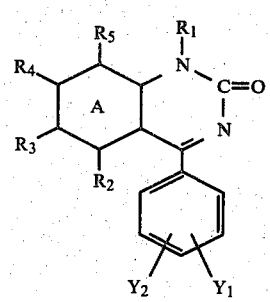

wherein $R_1$ represents $C_1$-$C_5$-alkyl, $C_3$-$C_6$-cycloalkyl, $C_3$-$C_6$-cycloalkyl-($C_1$-$C_4$)-alkyl, $C_1$-$C_5$-haloalkyl, allyl or propargyl, $R_2$, $R_3$, $R_4$ and $R_5$ represent independently of each other hydrogen, fluorine, chlorine, bromine, $C_1$-$C_4$-alkyl, $C_1$-$C_4$-alkoxy, $C_1$-$C_4$-alkylthio, nitro or trifluoromethyl, whereby at least two of $R_2$, $R_3$, $R_4$ and $R_5$ are hydrogen, $Y_1$ and $Y_2$ represent independently of each other hydrogen, fluorine, chlorine, bromine, $C_1$-$C_4$-alkyl, $C_1$-$C_4$-alkoxy or trifluoromethyl, and ring A has the structure

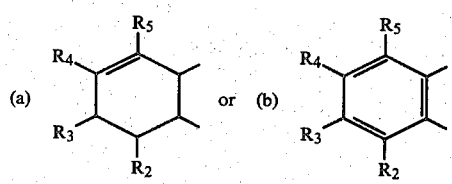

Various processes for the production of 4-phenyl-2(1H)-quinazolinones are known, e.g. that involving cyclisation of 2-amino-benzophenones. It has now however surprisingly been found that substantial increases in yield and reduction of costs can be achieved by initially preparing a quinazolindione and then introducing the desired phenyl radical.

The introduction of phenyl group occurs almost exclusively in the 4-position of the quinazolindione rather than equally between the 2- and 4-positions.

The invention therefore provides a process for the production of compounds of formula I as defined above by reacting a compound of formula II,

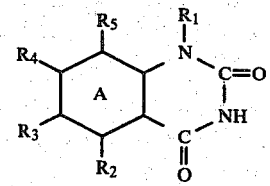

wherein $R_1$ to $R_5$ and A are as defined above, with a compound of formula III,

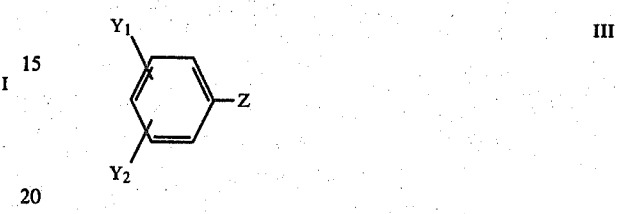

wherein $Y_1$ and $Y_2$ are as defined above, and Z represents lithium or a group of formula—MgX, wherein X represents chlorine, bromine or iodine, hydrolizing the resulting product and, if required, oxidising a product of formula I thus obtained wherein A has the structure (a) to produce a compound of formula I wherein A has the structure (b).

The reaction of II with III is suitably effected in an inert organic solvent, such as tetrahydrofurane, dioxane, dimethoxyethane, or diethylether and is conveniently carried out under anhydrous conditions and when required with an excess of the compound of formula III. Reaction temperatures conveniently lie between 0° and 60° C., preferably between 30° and 50° C. In a preferred embodiment the compound of formula II is initially treated with sodium hydride before reaction with a compound of formula III which need not then be in excess.

Hydrolysis of the reaction product may be carried out in conventional manner, e.g. with water, diluted mineral acids or weakly acidic compounds such as ammonium chloride or tartaric acid.

When hydrolysis of the reaction product, wherein A has the structure (a) is effected under weakly acidic or neutral conditions an intermediate compound of formula Ia,

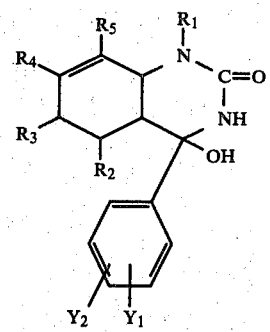

wherein $R_1$ to $R_5$, $Y_1$ and $Y_2$ are as defined above, can be obtained which reverts to a compound of formula I wherein A has the structure (a), e.g. on treatment with a dehydration agent.

The resulting compounds of formula I, wherein A has the structure (a) can be oxidized to compounds of formula I wherein A has the structure (b) for example with sulphur, selenium, a benzoquinone, tetracyanoethylene, triphenylmethyl perchlorate, or a catalyst such as palladium on charcoal, nickel or e.g. ferric oxide. A suitable temperature is from 200° to 210°. This reaction may, if desired, also be carried out in the presence of an inert organic solvent, such as o-dichlorobenzene, decaline or dodecylbenzene.

Compounds of formula II are new and also form part of the invention. They can be obtained by hydrolysing a compound of formula IV,

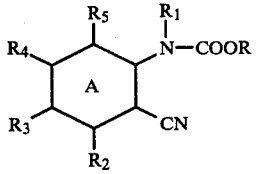

wherein A and $R_1$ to $R_5$ are as defined above, and R represents $C_1$-$C_4$-alkyl and, if required, oxidising a product of formula II thus obtained wherein A has the structure (a) to produce a compound of formula II wherein A has the structure (b).

The hydrolysis is conveniently carried out in an alkaline medium at room temperature. An alkalihydroxide, such as sodium or potassium hydroxide, e.g. ethanolic sodium hydroxide, is suitably used for this purpose. The reaction is however preferably carried out in the presence of hydrogen peroxide.

Oxidation can be carried out as described above for compounds of formula I.

The compounds of formula IV are new and also form part of the invention, they can be prepared by reacting a compound of formula V,

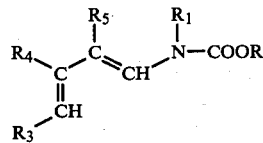

with a compound of formula VI,

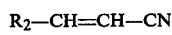

$R_2$—CH=CH—CN  VI wherein $R_1$ to $R_5$ and R are as defined above and, if required, oxidising a product of formula IV thus obtained wherein A has the structure (a) to produce a compound of formula IV wherein A has the structure (b).

The reaction of V and VI can be effected in presence or absence of a solvent at temperatures of e.g. between 120° and 140° C. Suitable solvents include o-dichlorobenzene, decaline and xylene.

The oxidation can be carried out as described above for compounds of formula I.

When oxidation of compounds of formulae I, II and IV wherein ring A has the structure (a) is required, it can conveniently be carried out without first isolating said compound.

The compounds of formula V may be prepared by reacting a compound of formula VII,

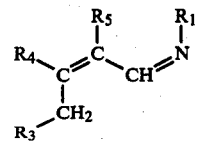

with a compound of formula VIII,

X'—COOR  VIII whereby $R_1$, $R_3$ to $R_5$ and R are as defined above and X' represents chlorine or bromine.

The reaction is suitably effected at room temperature in an inert organic solvent, such as benzene, toluene, hexane or methylene chloride. An acid binding agent, e.g. diethylaniline or 2,4,6-trimethylpyridine, may be used.

The compounds of formulae III, VI, VII and VIII are either known or may be produced in conventional manner. The end and intermediate products can be isolated and purified in conventional manner.

The compounds of formula I wherein A has the structure (b) are known e.g. from the German Offenlegungsschriften Nos. 1 695 769; 2 230 393; 1 805 501 and 2 307 808 and exhibit for example analgetic and anti-inflammatory activity.

The compounds of formula I wherein A has the structure (a) are new and also form part of the present invention.

In the compounds of formula I, when $R_1$ is alkyl, it is preferably isopropyl, when it is haloalkyl, it is preferably 2,2,2-trifluoroethyl, and when it is cycloalkylalkyl, it is preferably cyclopropylmethyl. The 4-position substituent is preferably phenyl or halophenyl, especially fluorophenyl, particularly 4-fluorophenyl.

A particularly preferred group of compounds of formula I is that of formula Ib,

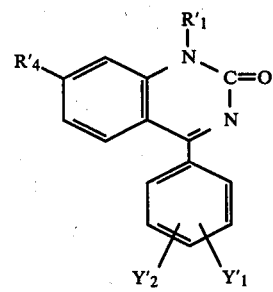

wherein
$R_1'$ represents $C_1$-$C_5$-alkyl, $C_3$-$C_6$-cycloalkyl, $C_3$-$C_6$-cycloalkyl-($C_1$-$C_4$)-alkyl, $C_1$-$C_5$-polyhaloalkyl, allyl or propargyl,
$R_4'$ represents hydrogen, fluorine, chlorine, bromine, $C_1$-$C_3$-alkyl or $C_1$-$C_3$-alkoxy or $C_1$-$C_3$-alkylthio, nitro or trifluoromethyl, and
$Y_1'$ and $Y_2'$ represent independently hydrogen, fluorine, chlorine, bromine, $C_1$-$C_4$-alkyl or $C_1$-$C_4$-alkoxy or trifluoromethyl with the proviso, that no more than one of $Y_1'$ and $Y_2'$ signifies trifluoromethyl.

Examples of compounds of the formula I which can be prepared according to the invention are 1-isopropyl-4-(4-fluorophenyl)-7-methyl-2(1H)-quinazolinone,
1-isopropyl-4-phenyl-2(1H)-quinazolinone,
1-isopropyl-4-phenyl-7-methyl-2(1H)-quinazolinone,
1-cyclopropylmethyl-4-phenyl-6-methoxy-2(1H)-quinazolinone and
1-(α-trifluoroethyl)-4-phenyl-6-chloro-2(1H)-quinazolinone.

The following examples illustrate the invention.

EXAMPLE 1

1-Isopropyl-4-phenyl-7-methyl-2(1H)-quinazolinone (a) N-Isopropyl-N-(3-methyl-1,3-butadienyl)-carbamic acid methyl ester To a stirred solution of 657 g diethylaniline in 2 l toluene is added dropwise over ca. 5 minutes 416 g methyl chloroformate. 500 g N-(3-methyl-2-butenyliden)-isopropylamine in 500 ml toluene are then added dropwise with stirring over 2 hours, maintaining the temperature between 25° and 30° C. Stirring is continued for 1 hour and the reaction mixture is then treated with 400 ml of water and 90 ml conc. hydrochloric acid. The organic phase is washed with 600 ml of saturated aqueous sodium bicarbonate solution and with 600 ml water, dried and evaporated in vacuo to give the title compound.

(b) 2-(N-Isopropyl-N-carbomethoxyamino)-4-methyl-benzonitrile 915 g N-isopropyl-N-(3-methyl-1,3-butadienyl)-carbamic acid methyl ester are heated without a solvent to 120° C. and 345 g acrylonitrile added dropwise. After completion of the addition the mixture is stirred for 1 hour at 140°. The resulting 2-(N-isopropyl-N-carbomethoxyamino)-4-methyl-3-cyclohexene-nitrile is heated at 200° and treated over a period of 2 hours portionwise with 386 g powdered sulphur. The reaction mixture is then stirred for 2 hours at 205° C. The resulting mixture is distilled under high vacuum at 110°–120° (0,1 torr), recrystallisation of the residue from benzine fraction yields the title product m.p. 100°–101°.

(c) 1-Isopropyl-7-methyl-quinazolin-2,4(1H,3H)-dione

To a suspension of 300 g 2-(N-isopropyl-N-carbomethoxyamino)-4-methyl-benzonitrile in 750 ml of ethanol and 234 ml 10N sodium hydroxide are added dropwise over 80 minutes 576 g of a 40% solution of hydrogen peroxide. The resulting clear solution is acidified with 195 ml of concentrated hydrochloric acid, whereupon the title compound precipitates, m.p. 250°–251°.

(d) 1-Isopropyl-4-phenyl-7-methyl-2(1H)-quinazolinone

To a suspension of 1.8 g sodium hydride in 25 ml tetrahydrofurane are added portionwise 13.08 g 1-isopropyl-7-methyl-quinazolin-2,4(1H,3H)-dione under constant release of hydrogen. 40 ml of a 2N solution of phenylmagnesiumbromide in tetrahydrofurane are added dropwise at 40° C. to the clear solution and the resulting suspension stirred at 40° for 15 hours. Water is added and the solvent is evaporated in vacuo. The residue is taken up with methylene chloride and 30 ml 12% hydrochloric acid. The organic layer is concentrated to give the title compound (recrystallized from toluene), m.p. 140°–143°.

By employing 40 ml of 2N p-fluorophenylmagnesiumbromide there is obtained 1-Isopropyl-4-(4-fluorophenyl)-7-methyl-2(1H)-quinazolinone, m.p. 174°–176°.

EXAMPLE 2

1-Isopropyl-4-(4-fluorophenyl)-7-methyl-2(1H)-quinazolinone (a) 1-Isopropyl-7-methyl-4a,5,6,8a-tetrahydro-2,4-(1H)-quinazolindione To a solution of 100 g 2-(N-isopropyl-N-carbomethoxyamino)-4-methyl-3-cyclohexene-nitrile in 700 ml 95% ethanol are added 90 ml of concentrated aqueous sodium hydroxide. To this mixture are added dropwise within 4 hours under stirring and at an internal temperature of 40° 600 ml 40% hydrogen peroxide. Stirring is continued over night at room temperature. The reaction mixture is concentrated in vacuo and the residue treated with water and toluene. The water layer is extracted twice with toluene and the combined toluene extracts are washed with water and evaporated in vacuo to give the title compound.

(b) 1-Isopropyl-4-(4-fluorophenyl)-7-methyl-4a,5,6,8a-tetrahydro-2(1H)-quinazolinone To a stirred suspension of 2.37 g sodium hydride in 45 ml tetrahydrofurane are added portionwise at room temperature 13.32 g 1-isopropyl-7-methyl-4a,5,6,8a-tetrahydro-2,4-(1H)-quinazolindione and the mixture stirred for 45 minutes. 39 ml of a 2N solution of 4-fluorophenyl magnesium bromide in tetrahydrufurane are then added dropwise within 2 hours at an internal temperature of 40° and the resulting suspension stirred at 40° for 15 hours. 23 ml 15% hydrochloric acid are then added under ice cooling and the solvent removed in vacuo. The residue is taken up with water and methylene chloride. The methylene chloride phase is evaporated to dryness to obtain the title compound.

When aqueous ammonium chloride is used in place of 15% hydrochloric acid 1-isopropyl-4-(4-fluorophenyl)-4-hydroxy-7-methyl-4a,5,6,8a-tetrahydro-2(1H)-quinazolinone, m.p. 154°–158° is obtained which, when treated with hydrochloric acid reverts to the title compound.

(c) 1-Isopropyl-4-(4-fluorophenyl)-7-methyl-2(1H)-quinazolinone 17.4 g 1-isopropyl-4-(4-fluorophenyl)-7-methyl-4a,5,6,8a-tetrahydro-2(1H)-quinazolinone are dissolved under heating in 50 ml decaline and treated portionwise at 140° with 4 g powdered sulphur. On completion of the addition stirring is continued for 1 hour at 160°. The mixture is diluted with toluene and extracted several times with 15% hydrochloric acid. The acidic phase is treated with methylene chloride and neutralized under ice cooling with sodium hydroxide solution. The water phase is extracted with methylene chloride and the combined methylene chloride extracts concentrated in vacuo. The concentrate is chromatographed on silica gel using dichloromethane and methanol as eluant. After recrystallisation from toluene the title compound is obtained, m.p. 174°–176°.

What I claim is:

1. A compound of the formula:

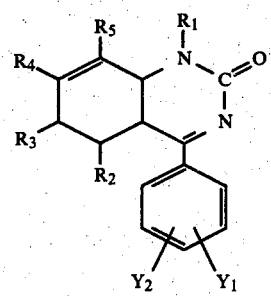

wherein

R₁ is $C_1$–$C_5$-alkyl, $C_3$–$C_6$-cycloalkyl, $C_3$–$C_6$-cycloalkyl-($C_1$–$C_4$)-alkyl, $C_1$–$C_5$-haloalkyl, allyl or propargyl, R₂, R₃, R₄ and R₅ are independently of each other hydrogen, fluorine, chlorine, bromine, $C_1$–$C_4$-alkyl, $C_1$–$C_4$-alkoxy, $C_1$–$C_4$-alkylthio, nitro or trifluoromethyl, whereby at least two of R₂, R₃, R₄ and R₅ are hydrogen, and Y₁ and Y₂ are independently of each other hydrogen, fluorine, chlorine, bromine, $C_1$–$C_4$-alkyl, $C_1$–$C_4$-alkoxy or trifluoromethyl.

2. A compound of claim 1 in which Y₁ is hydrogen or fluoro and Y₂ is hydrogen and R₁ is isopropyl, 2,2,2-trifluoroethyl or cyclopropylmethyl.

3. A compound of claim 2 in which R₁ is isopropyl, R₄ is methyl and R₂, R₃ and R₅ are each hydrogen.

4. A compound of the formula:

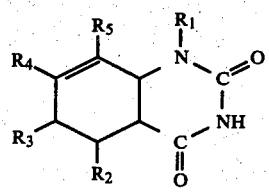

wherein

R₁ is $C_1$–$C_5$-alkyl, $C_3$–$C_6$-cycloalkyl, $C_3$–$C_6$-cycloalkyl-($C_1$–$C_4$)-alkyl, $C_1$–$C_5$-haloalkyl, allyl or propargyl, and R₂, R₃, R₄ and R₅ are independently of each other hydrogen, fluorine, chlorine, bromine, $C_1$–$C_4$-alkyl, $C_1$–$C_4$-alkoxy, $C_1$–$C_4$-alkylthio, nitro or trifluoromethyl, whereby at least two of R₂, R₃, R₄ and R₅ are hydrogen.

5. A compound of claim 4 in which R₁ is isopropyl, 2,2,2-trifluoroethyl or cyclopropylmethyl.

6. A compound of claim 5 in which R₁ is isopropyl, R₄ is methyl and R₂, R₃ and R₅ are each hydrogen.

7. A compound of the formula:

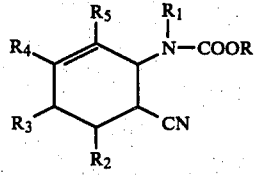

wherein

R is $C_1$–$C_4$-alkyl,

R₁ is $C_1$–$C_5$-alkyl, $C_3$–$C_6$-cycloalkyl, $C_3$–$C_6$-cycloalkyl-($C_1$–$C_4$)-alkyl, $C_1$–$C_5$-haloalkyl, allyl or propargyl, and R₂, R₃, R₄ and R₅ are independently of each other hydrogen, fluorine, chlorine, bromine, $C_1$–$C_4$-alkyl, $C_1$–$C_4$-alkoxy, $C_1$–$C_4$-alkylthio, nitro or trifluoromethyl, whereby at least two of R₂, R₃, R₄ and R₅ are hydrogen.

8. A compound of claim 7 in which R₁ is isopropyl, 2,2,2-trifluoromethyl or cyclopropylmethyl.

9. A compound of claim 8 in which R₁ is isopropyl, R₄ is methyl and R₂, R₃ and R₅ are each hydrogen.

* * * * *